US012678420B2

(12) United States Patent
Kirsch et al.

(10) Patent No.: US 12,678,420 B2
(45) Date of Patent: Jul. 14, 2026

(54) SOLID ORAL PHARMACEUTICAL COMPOSITIONS INCLUDING ALKYL 3,4,5-TRIHYDROXYBENZOATE AS A NITROSAMINE INHIBITOR

(71) Applicant: Mylan Pharmaceuticals Inc., Canonsburg, PA (US)

(72) Inventors: John D. Kirsch, Waynesburg, PA (US); Ross A. Friedman, Washington, PA (US)

(73) Assignee: Mylan Pharmaceuticals Inc., Morgatown, WV (US)

( * ) Notice: Subject to any disclaimer, the term of this patent is extended or adjusted under 35 U.S.C. 154(b) by 342 days.

(21) Appl. No.: 18/432,291

(22) Filed: Feb. 5, 2024

(65) Prior Publication Data

US 2024/0269103 A1 Aug. 15, 2024

Related U.S. Application Data

(60) Provisional application No. 63/443,792, filed on Feb. 7, 2023.

(51) Int. Cl.

| | |
|---|---|
| ***A61K 31/235*** | (2006.01) |
| ***A61K 9/00*** | (2006.01) |
| ***A61K 9/20*** | (2006.01) |
| ***A61K 31/135*** | (2006.01) |

(52) U.S. Cl.

CPC .......... *A61K 31/235* (2013.01); *A61K 9/0053* (2013.01); *A61K 9/2054* (2013.01); *A61K 31/135* (2013.01)

(58) Field of Classification Search

CPC .................................................... A61K 31/235

See application file for complete search history.

(56) References Cited

U.S. PATENT DOCUMENTS

| | | | |
|---|---|---|---|
| 7,067,555 | B2 | 6/2006 | Harper et al. |
| 2014/0178511 | A1 | 6/2014 | Kirsch et al. |

FOREIGN PATENT DOCUMENTS

| | | | |
|---|---|---|---|
| EP | 4169516 | A1 | 4/2023 |

OTHER PUBLICATIONS

Homšak et al., "Assessment of a Diverse Array of Nitrite Scavengers in Solution and Solid State: A Study of Inhibitory Effect on the Formation of Alkyl-Aryl and Dialkyl N-Nitrosamine Derivatives", Processes, 2022, 18 pages, vol. 10.

*Primary Examiner* — Golam M Shameem

(57) ABSTRACT

The present invention relates to a solid oral pharmaceutical composition that includes: (a) an active pharmaceutical ingredient; (b) a nitrosamine inhibitor that includes linear or branched $C_1$-$C_{10}$ alkyl 3,4,5-trihydroxybenzoate; and (c) a pharmaceutically acceptable excipient. At least one of: (i) the active pharmaceutical ingredient includes at least one covalently bonded amine group that is subject to conversion to nitrosamine; or (ii) the solid oral pharmaceutical composition includes at least one amine, that is other than the amine group covalently bonded to/within the active pharmaceutical ingredient, and which is subject to conversion to nitrosamine. The nitrosamine inhibitor is present in an amount at least sufficient to reduce the amount of nitrosamine formed in the solid oral pharmaceutical composition, compared to the amount of nitrosamine formed in a comparative solid oral pharmaceutical composition that is free of the nitrosamine inhibitor.

15 Claims, 4 Drawing Sheets

SOLID ORAL PHARMACEUTICAL COMPOSITIONS INCLUDING ALKYL 3,4,5-TRIHYDROXYBENZOATE AS A NITROSAMINE INHIBITOR

CROSS-REFERENCE TO RELATED APPLICATION

The present application claims priority to U.S. Provisional Application Ser. No. 63/443,792, entitled "Solid Oral Pharmaceutical Compositions Including Alkyl 3,4,5-Trihydroxybenzoate as a Nitrosamine Inhibitor" filed Feb. 7, 2023, the entire disclosure of which is hereby incorporated by reference.

FIELD

The present invention relates to solid oral pharmaceutical compositions that include an active pharmaceutical ingredient, a nitrosamine inhibitor that includes linear or branched $C_1$-$C_{10}$ alkyl 3,4,5-trihydroxybenzoate, and a pharmaceutically acceptable excipient, where the nitrosamine inhibitor is present in an amount at least sufficient to reduce the amount of nitrosamine formed in the solid oral pharmaceutical composition, compared to the amount of nitrosamine formed in a comparative solid oral pharmaceutical composition that is free of the nitrosamine inhibitor.

BACKGROUND

Solid oral pharmaceutical compositions can be subject to the formation of nitrosamines over time, such as during storage and/or shipment thereof. Nitrosamines are considered to be undesirable contaminants due to the potential mutagenic effects associated therewith. Nitrosamines typically form from secondary aliphatic amines, and in some instances at slower rates from tertiary aliphatic amines. Sources of nitrosamine formation include, active pharmaceutical agents that have at least one amine group covalently bonded thereto/therein that is subject to conversion to nitrosamine, and/or at least one amine present within the solid oral pharmaceutical composition, that is not covalently bonded to/within the active pharmaceutical agent, and which is subject to conversion to nitrosamine. Formation of nitrosamines also typically involves the presence of a nitrosating agent, such as nitrite ($NO_2^-$) and/or dinitrogen trioxide ($N_2O_3$).

It would be desirable to develop new solid oral pharmaceutical compositions that have reduced levels of nitrosamine formation. It would be further desirable that such newly developed solid oral pharmaceutical compositions include additives that meet regulatory requirements, such as, but not limited to, maximum daily exposure requirements.

SUMMARY

In accordance with the present invention, there is provided a solid oral pharmaceutical composition comprising: (a) an active pharmaceutical ingredient; (b) a nitrosamine inhibitor comprising linear or branched $C_1$-$C_{10}$ alkyl 3,4,5-trihydroxybenzoate; and (c) a pharmaceutically acceptable excipient. With the solid oral pharmaceutical compositions, at least one of: (i) the active pharmaceutical ingredient comprises at least one covalently bonded amine group that is subject to conversion to nitrosamine; and/or (ii) the solid oral pharmaceutical composition comprises at least one amine, that is other than the amine group covalently bonded to/within the active pharmaceutical ingredient, and which is subject to conversion to nitrosamine. The nitrosamine inhibitor is present in an amount at least sufficient to reduce the amount of nitrosamine formed in the solid oral pharmaceutical composition, compared to the amount of nitrosamine formed in a comparative solid oral pharmaceutical composition that is free of the nitrosamine inhibitor.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWINGS

In FIGS. 1 through 4 like characters and headings refer to the same components and/or have the same meanings, as the case may be, unless otherwise stated.

DETAILED DESCRIPTION

Figure 1:
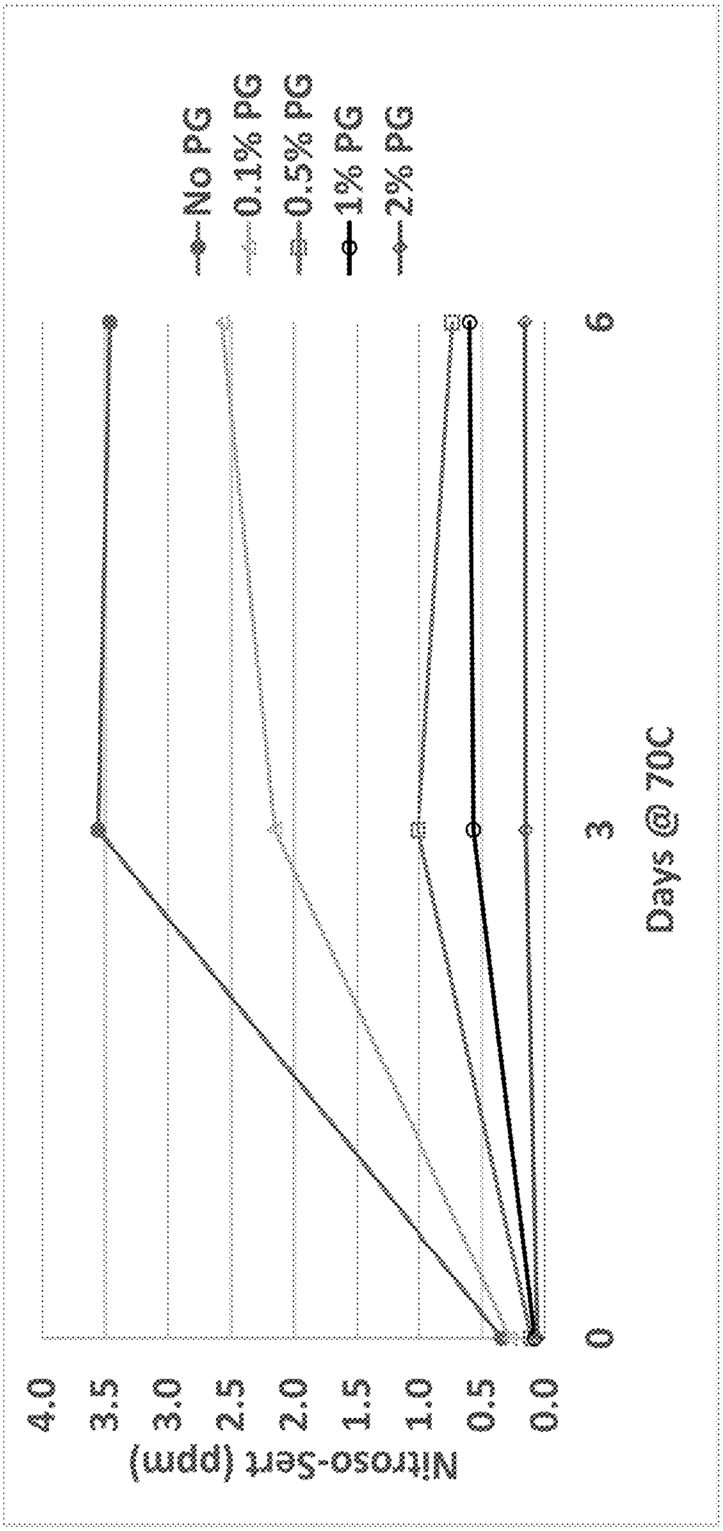
FIG. 1 is a graphical representation of a plot of nitrososertraline formed in a comparative solid oral pharmaceutical composition and solid oral pharmaceutical compositions according to the present invention as a function of time, and as described in further detail in the Examples.

As used herein, the articles "a," "an," and "the" include plural referents unless otherwise expressly and unequivocally limited to one referent.

Unless otherwise indicated, all ranges or ratios disclosed herein are to be understood to encompass any and all values, and subranges or subratios subsumed therein. For example, a stated range or ratio of "1 to 10" should be considered to include: any and all values there-between, including the stated terminal values (such as 1, 2, 3, 4, 5, 6, 7, 8, 9, and 10); and subranges between (and inclusive of) the minimum value of 1 and the maximum value of 10, that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

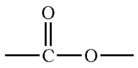

or

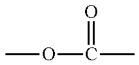, equivalently —C(O)O—, is inclusive of the right-to-left representation thereof, or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term “about.”

As used herein, “at least one of” is synonymous with “one or more of,” whether the elements are listed conjunctively or disjunctively. For example, the phrases “at least one of A, B, and C” and “at least one of A, B, or C” each mean any one of A, B, or C, or any combination of any two or more of A, B, or C. For example, A alone; or B alone; or C alone; or A and B; or A and C; or B and C; or all of A, B, and C.

As used herein, “selected from” is synonymous with “chosen from” whether the elements are listed conjunctively or disjunctively. Further, the phrases “selected from A, B, and C” and “selected from A, B, or C” each mean any one of A, B, or C, or any combination of any two or more of A, B, or C. For example, A alone; or B alone; or C alone; or A and B; or A and C; or B and C; or all of A, B, and C.

All documents, such as but not limited to issued patents and patent applications, referred to herein, and unless otherwise indicated, are to be considered to be “incorporated by reference” in their entirety.

As used herein, the term “aliphatic group” and similar terms, such as “aliphatic substituent” means linear or branched aliphatic groups and/or cycloaliphatic groups, which are not aromatic, and which optionally include at least one carbon-carbon unsaturated linkage, such as at least one alkene linkage (—C═C—) and/or at least one alkyne linkage (—C≡C—). With some embodiments, linear or branched aliphatic groups herein include 1 to 10 carbon atoms, and cycloaliphatic groups include 3 to 10 carbon atoms.

As used herein, recitations of “linear or branched” groups, such as linear or branched alkyl, are herein understood to include: a methylene group or a methyl group; groups that are linear, such as linear $C_2$-$C_{10}$ alkyl groups; and groups that are appropriately branched, such as branched $C_3$-$C_{10}$ alkyl groups.

The term “alkyl” as used herein means linear or branched, cyclic or acyclic $C_1$-$C_{10}$ alkyl. Linear or branched alkyl can include $C_1$-$C_{10}$ alkyl, such as $C_1$-$C_5$ alkyl, such as $C_2$-$C_5$ alkyl, such as $C_2$-$C_4$ alkyl. Examples of alkyl groups from which the various alkyl groups of the present invention can be selected from, include, but are not limited to, those recited further herein. Alkyl groups can include “cycloalkyl” groups. The term “cycloalkyl” as used herein means groups that are appropriately cyclic, such as, but not limited to, $C_3$-$C_{10}$ cycloalkyl (including, but not limited to, cyclic $C_3$-$C_8$ alkyl, or cyclic $C_5$-$C_7$ alkyl) groups.

Representative alkyl groups include, but are not limited to, methyl, ethyl, propyl, isopropyl, butyl, isobutyl, sec-butyl, tert-butyl, pentyl, neopentyl, hexyl, heptyl, octyl, nonyl, and decyl. Representative cycloalkyl groups include, but are not limited to, cyclopropyl, cyclobutyl, cyclopentyl, cyclohexyl, and cyclooctyl.

As used herein, the term “nitrosamine” and similar terms such as “nitrosamines,” “nitrosamine group,” and “nitrosamine groups” are inclusive of and interchangeable with “N-nitrosamine,” “N-nitrosamines,” “N-nitrosamine group,” and “N-nitrosamine groups.”

In accordance with some embodiments of the present invention, nitrosamines, the formation of which is reduced with the present solid oral pharmaceutical compositions, are represented by the following Formula (A).

(Formula (A)

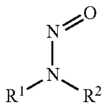

With reference to Formula (A), $R^1$ and $R^2$ are each independently an aliphatic group, such as a linear or branched aliphatic group, such as an alkyl group, such as a linear or branched $C_1$-$C_{10}$ alkyl group, or a cycloaliphatic group, such as a $C_3$-$C_{10}$ cycloalkyl group. With some embodiments, $R^1$ and $R^2$ together form a cyclic group, such as a cycloaliphatic group including from 2 to 10 carbon atoms, such as 2 to 10 methylene groups ($—CH_2—$). In accordance with some further embodiments: $R^1$ is a linear or branched $C_1$-$C_{10}$ alkyl group, or a $C_3$-$C_{10}$ cycloalkyl group; and $R^2$ is an active pharmaceutical ingredient, in which case the nitrosamine group is part of the active pharmaceutical ingredient, which with some embodiments is referred to as a N-nitrosamine active pharmaceutical ingredient. In accordance with some additional embodiments, $R^1$ and $R^2$ together form a cyclic group, such as a cycloaliphatic group, including from 2 to 10 carbon atoms, such as 2 to 10 methylene groups ($—CH_2—$), in which the cyclic ring thereof is fused to and/or bonded (e.g., by a single bond) to at least one other ring (not shown), such as a cycloaliphatic ring and/or an aromatic ring, of the active pharmaceutical ingredient, which with some embodiments is referred to as a N-nitrosamine active pharmaceutical ingredient.

The solid oral pharmaceutical compositions of the present invention include an active pharmaceutical ingredient. With some embodiments, the active pharmaceutical ingredient includes at least one covalently bonded amine group that is subject to conversion to nitrosamine. The covalently bonded amine groups of the active pharmaceutical ingredient, with some embodiments, are each independently a secondary aliphatic amine. With some further embodiments, the covalently bonded amine groups of the active pharmaceutical ingredient are each independently selected from amine groups represented by the following Formulas (B) and (C)

Formula (B)

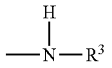

With reference to Formula (B), $R^3$ is an aliphatic group, such as a linear or branched aliphatic group, such as an alkyl group, such as a linear or branched $C_1$-$C_{10}$ alkyl group, or a cycloaliphatic group, such as a $C_3$-$C_{10}$ cycloalkyl group. The amine group represented by Formula (B) is covalently bonded to and extends from the active pharmaceutical ingredient.

Formula (C)

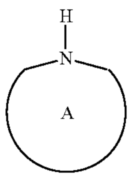

With reference to Formula (C), Ring A is a cycloaliphatic ring, such as a $C_3$-$C_{10}$ cycloalkyl ring, which is typically fused to and/or covalently bonded (e.g., by a single bond) to at least one other ring (not shown), such as a cycloaliphatic ring and/or an aromatic ring, of the active pharmaceutical ingredient.

The solid oral pharmaceutical composition, with some embodiments, includes at least one amine, that is other than the covalently bonded amine of the active pharmaceutical ingredient, and which is subject to conversion to nitrosamine, and which is referred to herein and with some embodiments as a free amine. The free amine of the solid oral pharmaceutical composition, with some embodiments, is present in/with the pharmaceutically acceptable excipient and/or the active pharmaceutical ingredient. The free amine, with some embodiments, is an aliphatic amine, such as a linear or branched aliphatic amine, and/or a cycloaliphatic amine. With some further embodiments, the free amine is a secondary aliphatic amine. The free amine, with some embodiments, is represented by the following Formula (D).

Formula (D)

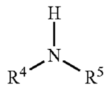

With reference to Formula (D), $R^4$ and $R^5$ are each independently an aliphatic group, such as a linear or branched aliphatic group, such as an alkyl group, such as a linear or branched $C_1$-$C_{10}$ alkyl group, or a cycloaliphatic group, such as a $C_3$-$C_{10}$ cycloalkyl group. With some embodiments, $R^4$ and $R^5$ together form a cyclic group, such as a cycloaliphatic group including from 2 to 10 carbon atoms, such as 2 to 10 methylene groups ($-CH_2-$).

The active pharmaceutical ingredient, of the solid oral pharmaceutical compositions of the present invention, includes synthetic and/or natural active pharmaceutical ingredients, and/or pharmaceutically acceptable salts thereof. Pharmaceutically acceptable salts of the active pharmaceutical ingredient, include but are not limited to HCl salts thereof. General classes of active pharmaceutical ingredients include, but are not limited to: analgesics; hypertension drugs, such as angiotensin II receptor blockers (ARBs), such as sartans, such as azilsartan, candesartan, irbesartan, olmesartan, losartan, valsartan, telmisartan, and eprosartan; further hypertension drugs, such as beta blockers, such as propranolol, sotalol, acebutalol, metoprolol, atenolol, and labetolol; histamine H2-receptor antagonists (or histamine-2 blockers), such a cimetidine, ranitidine, nizatidine, and famotidine; antidepressants, such as selective serotonin reuptake inhibitors (SSRIs), such a sertraline, citalopram, dapoxetine, escitalopram, fluoxetine, fluvoxamine, paroxetine, and vortioxetine.

With some embodiments, the active pharmaceutical ingredient includes at least one of an angiotensin II receptor blocker, a histamine H2-receptor antagonist, a selective serotonin reuptake inhibitor, and/or pharmaceutically acceptable salts of each thereof.

The active pharmaceutical ingredient, with some embodiments of the present invention, includes at least one covalently bonded amine group that is subject to conversion to nitrosamine.

In accordance with some further embodiments, the active pharmaceutical ingredient includes at least one of sertraline, or a pharmaceutically acceptable salt of sertraline.

Sertraline can be represented by the following Formula (Ia),

Formula (Ia)

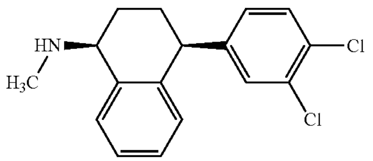

The chemical name for sertraline, as represented by Formula (Ia), is (1S,4S)-4-(3,4-dichlorophenyl)-N-methyl-1,2,3,4-tetrahydronaphthalen-1-amine.

The following Formula (Ib) is a representative structure for N-nitroso sertraline, Formula (Ib)

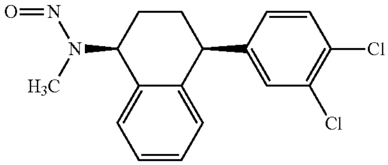

The chemical name for the N-nitroso sertraline, as represented by Formula (Ib), is N-((1S,4S)-4-(3,4-dichlorophenyl)-1,2,3,4-tetrahydronaphthalen-1-yl)-N-methylnitrous amide.

The active pharmaceutical ingredient is present in the solid oral pharmaceutical composition, in any suitable amount, such as a pharmaceutically effective amount. With some embodiments, the active pharmaceutical ingredient is present in the solid oral pharmaceutical composition in an amount of from 10 to 60 percent by weight, or from 20 to 50 percent by weight, or from 30 to 40 percent by weight, the percent weights in each case being based on the total weight of the solid oral pharmaceutical composition.

The nitrosamine inhibitor, of the solid oral pharmaceutical compositions of the present invention, includes at last one alkyl 3,4,5-trihydroxybenzoate, such as a linear or branched $C_1$-$C_{10}$ alkyl 3,4,5-trihydroxybenzoate, or a linear or branched $C_2$-$C_5$ alkyl 3,4,5-trihydroxybenzoate. With some embodiments, the alkyl 3,4,5-trihydroxybenzoate can be represented by the following Formula (II), Formula (II)

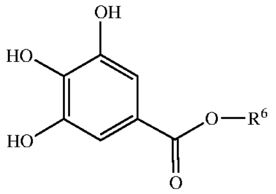

With reference to Formula (II), $R^6$ is a linear or branched $C_1$-$C_{10}$ alkyl group, such as a linear or branched $C_2$-$C_5$ alkyl group. With some embodiments of the present invention, $R^6$ of Formula (II), is an n-propyl or iso-propyl group.

The alkyl 3,4,5-trihydroxybenzoate can also be referred to as an alkyl gallate, such as a linear or branched $C_1$-$C_{10}$ alkyl gallate, or a linear or branched $C_2$-$C_5$ alkyl gallate.

With some embodiments of the present invention, the nitrosamine inhibitor includes n-propyl 3,4,5-trihydroxybenzoate (or n-propyl gallate).

In accordance with some embodiments, the nitrosamine inhibitor, of the solid oral pharmaceutical compositions of the present invention, consists essentially of at last one alkyl 3,4,5-trihydroxybenzoate, such as a linear or branched $C_1$-$C_{10}$ alkyl 3,4,5-trihydroxybenzoate, or a linear or branched $C_2$-$C_5$ alkyl 3,4,5-trihydroxybenzoate. In accordance with some embodiments, the nitrosamine inhibitor, of the solid oral pharmaceutical compositions of the present invention, consists of at last one alkyl 3,4,5-trihydroxybenzoate, such as a linear or branched $C_1$-$C_{10}$ alkyl 3,4,5-trihydroxybenzoate, or a linear or branched $C_2$-$C_5$ alkyl 3,4,5-trihydroxybenzoate.

In accordance with the present invention, the nitrosamine inhibitor is present in an amount at least sufficient to reduce the amount of nitrosamine formed in the solid oral pharmaceutical composition, compared to the amount of nitrosamine formed in a comparative solid oral pharmaceutical composition that is free of the nitrosamine inhibitor.

As used herein, the recitation of "a comparative solid oral pharmaceutical composition that is free of the nitrosamine inhibitor" means a comparative composition that includes the same active pharmaceutical ingredient, the same pharmaceutically acceptable excipient, in the same relative amounts, does not include the nitrosamine inhibitor, and which is prepared and evaluated under the same conditions, as the solid oral pharmaceutical composition according to the present invention.

The amount of nitrosamine formed in the inventive and comparative solid oral pharmaceutical compositions can be determined in accordance with art-recognized analytical methods. With some embodiments, the amount of nitrosamine formed in the inventive and comparative solid oral pharmaceutical compositions is determined using liquid chromatography-mass spectrometry (LC-MS).

In accordance with some embodiments, shortly after preparation of the inventive and comparative solid oral pharmaceutical compositions, an initial (or to) amount (or level) of nitrosamine is determined. The inventive and comparative solid oral pharmaceutical compositions are then typically subjected to accelerated testing under controlled conditions of elevated temperature, such as 50° C. or 70° C., and relative humidity (RH), such as 70% RH or 75% RH. Test samples are typically withdrawn and analyzed to determine the amount of nitrosamine formed, over a period of time, such as days (e.g., 3, 6, and/or 30 days).

In accordance with some embodiments, the reduction in the amount of nitrosamine formed in the inventive solid oral pharmaceutical compositions, over a period of time, is characterized as a percent reduction relative to the amount of nitrosamine formed in a comparative solid oral pharmaceutical composition, which is calculated using the following Equation-(1):

$$100\times\left\{\frac{(\text{comparative amount of nitrosamine formed at } t_x) - (\text{inventive amount of nitrosamine formed at } t_x)}{(\text{comparative amount of nitrosamine formed at } t_x)}\right\} \quad \text{Equation-(1)}$$

With reference to Equation-(1), the "comparative amount of nitrosamine formed at $t_x$" means the amount of nitrosamine formed in the comparative solid oral pharmaceutical composition at time $t_x$. With further reference to Equation-(1), the "inventive amount of nitrosamine formed at $t_x$" means the amount of nitrosamine formed in the solid oral pharmaceutical composition according to the present invention at time $t_x$.

With some embodiments of the present invention, the amount of nitrosamine formed in the solid oral pharmaceutical composition according to the present invention is reduced by at least 10 percent by weight, or at least 20 percent by weight, or at least 30 percent by weight, or at least 40 percent by weight, or at least 50 percent by weight, in each case as compared to the amount of nitrosamine formed in the comparative solid oral pharmaceutical composition that is free of said nitrosamine inhibitor, in each case under the same test and environmental conditions, and for the same period of time.

With some further embodiments of the present invention, the amount of nitrosamine formed in the solid oral pharmaceutical composition according to the present invention is reduced by at least 75 percent by weight, compared to the amount of nitrosamine formed in the comparative solid oral pharmaceutical composition that is free of said nitrosamine inhibitor, in each case under the same test and environmental conditions, and for the same period of time.

With some further embodiments of the present invention, the amount of nitrosamine formed in the solid oral pharmaceutical composition according to the present invention is reduced by at least 80 percent by weight, or at least 85 percent by weight, or at least 90 percent by weight, or at least 95 percent by weight, in each case as compared to the amount of nitrosamine formed in the comparative solid oral pharmaceutical composition that is free of said nitrosamine inhibitor, in each case under the same test and environmental conditions, and for the same period of time.

With some further embodiments of the present invention, the amount of nitrosamine formed in the solid oral pharmaceutical composition according to the present invention is reduced by from 92 percent by weight to less than or equal to 100 percent by weight, or by 93 percent by weight to less than or equal to 98 percent by weight, compared to the amount of nitrosamine formed in the comparative solid oral pharmaceutical composition that is free of said nitrosamine inhibitor, in each case under the same test and environmental conditions, and for the same period of time.

The nitrosamine inhibitor can be present in the solid oral pharmaceutical composition according to the present invention in any amount, provided such amount is at least sufficient so as to reduce the amount of nitrosamine formed in the solid oral pharmaceutical composition, compared to the amount of nitrosamine formed in a comparative solid oral pharmaceutical composition that is free of said nitrosamine inhibitor.

With some embodiments, the nitrosamine inhibitor is present in an amount of at least 0.05 percent by weight, based on weight of the active pharmaceutical ingredient.

With some further embodiments, the nitrosamine inhibitor is present in an amount of from 0.05 percent by weight to 4 percent by weight, or from 0.05 percent by weight to 3 percent by weight, or from 0.05 percent by weight to 2.5 percent by weight, based on weight of the active pharmaceutical ingredient, inclusive of the recited amounts.

With some additional embodiments of the present invention, the nitrosamine inhibitor is present in an amount of from 0.5 percent by weight to 3 percent by weight, or from 0.5 percent by weight, to 2.5 percent by weight, based on weight of the active pharmaceutical ingredient, inclusive of the recited amounts.

The nitrosamine inhibitor, with some embodiments, is introduced into the solid oral pharmaceutical composition by at least one of an intra-granular addition method and/or an extra-granular addition method. Any art-recognized intra-granular addition method, and any art-recognized extra-granular addition method can be used.

The solid oral pharmaceutical compositions of the present invention include at least one pharmaceutically acceptable excipient. Classes of pharmaceutically acceptable excipients include, but are not limited to: diluents, such as sugar compounds, such as lactose, dextrin, glucose, sucrose, and sorbitol, and/or inorganic compounds, such as silicates, calcium salts, magnesium salts, sodium chloride, and potassium chloride; binders, compression aids, and granulating agents, such as natural and/or synthetic polymers, such as starches, polymeric sugars, sugar alcohol, and cellulose derivatives; disintegrants, such as starch, cellulose derivatives, alginates, and crospovidone (cross-linked polyvinylpyrrolidone); glidants, such as anhydrous silicon and other silica compounds; and lubricants, such as stearic acid and salts of stearic acid.

With some embodiments, the pharmaceutically acceptable excipient includes at least one of microcrystalline cellulose, sucrose, hydroxypropyl cellulose, hydroxypropyl methylcellulose, sodium starch glycolate, starch, xylitol, fructose, sorbitol, calcium phosphate, calcium sulfate, magnesium stearate, oleic acid, stearic acid, stearyl alcohol, calcium carbonate, dextrose, lactose, polyvinylpyrrolidone, crosslinked polyvinylpyrrolidone, silica, titanium dioxide, gelatin, or triglercerides.

The pharmaceutically acceptable excipient(s) can be present in the solid oral pharmaceutical compositions of the present invention in any suitable amount. With some embodiments, the pharmaceutically acceptable excipient is present in an amount of from 0.05 to 99.5 percent by weight, or from 5 to 95 percent by weight, or from 10 to 90 percent by weight, the percent weights in each case being based on the total weight of the solid oral pharmaceutical composition.

The solid oral pharmaceutical compositions of the present invention can be in any suitable form. With some embodiments, the solid oral pharmaceutical composition of the present invention is in a form selected from tablets, capsules, and free flowing granules. The solid oral pharmaceutical compositions of the present invention can be formed into tablets, capsules, and/or free flowing granules in accordance with art-recognized methods.

The present invention can be further characterized by one or more of the following non-limiting clauses.

Clause 1: A solid oral pharmaceutical composition comprising:

(a) an active pharmaceutical ingredient;

(b) a nitrosamine inhibitor comprising linear or branched $C_1$-$C_{10}$ alkyl 3,4,5-trihydroxybenzoate; and (c) a pharmaceutically acceptable excipient, wherein at least one of, (i) the active pharmaceutical ingredient comprises at least one covalently bonded amine group that is subject to conversion to nitrosamine; or (ii) the solid oral pharmaceutical composition comprises at least one amine that is subject to conversion to nitrosamine, and wherein the nitrosamine inhibitor is present in an amount at least sufficient to reduce the amount of nitrosamine formed in the solid oral pharmaceutical composition, compared to the amount of nitrosamine formed in a comparative solid oral pharmaceutical composition that is free of the nitrosamine inhibitor.

Clause 2: The solid oral pharmaceutical composition of clause 1, wherein the active pharmaceutical ingredient comprises at least one of, an angiotensin II receptor blocker, a beta-blocker, a histamine H2-receptor antagonist, a selective serotonin reuptake inhibitor, or pharmaceutically acceptable salts of one or more thereof.

Clause 3: The solid oral pharmaceutical composition of clauses 1 or 2, wherein the active pharmaceutical ingredient comprises at least one covalently bonded amine group that is subject to conversion to nitrosamine.

Clause 4: The solid oral pharmaceutical composition of any one of clauses 1 to 3, wherein the active pharmaceutical ingredient comprises at least one of sertraline, or a pharmaceutically acceptable salt of sertraline.

Clause 5: The solid oral pharmaceutical composition of any one of clauses 1 to 4, wherein the nitrosamine inhibitor comprises or branched $C_2$-$C_5$ alkyl 3,4,5-trihydroxybenzoate.

Clause 6: The solid oral pharmaceutical composition of any one of clauses 1 to 5, wherein the nitrosamine inhibitor comprises n-propyl 3,4,5-trihydroxybenzoate.

Clause 7: The solid oral pharmaceutical composition of any one of clauses 1 to 6, wherein the amount of the nitrosamine inhibitor is at least 0.05 percent by weight, based on weight of the active pharmaceutical ingredient.

Clause 8: The solid oral pharmaceutical composition of any one of clauses 1 to 7, wherein the amount of the nitrosamine inhibitor is from 0.05 percent by weight to 4 percent by weight, or from 0.05 percent by weight to 3 percent by weight, or from 0.05 percent by weight to 2.5 percent by weight, based on weight of the active pharmaceutical ingredient.

Clause 9: The solid oral pharmaceutical composition of ay one of clauses 1 to 8, wherein, the amount of the nitrosamine inhibitor is from 0.5 percent by weight to 3 percent by weight, or from 0.5 percent by weight to 2.5 percent by weight, based on weight of the active pharmaceutical ingredient.

Clause 10: The solid oral pharmaceutical composition of any one of clauses 1 to 8, wherein the amount of nitrosamine formed in the solid oral pharmaceutical composition is reduced by at least 10 percent by weight, or at least 20 percent by weight, or at least 30 percent by weight, or at least 40 percent by weight, or at least 50 percent by weight, in each case as compared to the amount of nitrosamine formed in the comparative solid oral pharmaceutical composition that is free of said nitrosamine inhibitor.

Clause 11: The solid oral pharmaceutical composition of any one of clauses 1 to 10, wherein the amount of nitrosamine formed in the solid oral pharmaceutical composition is reduced by at least 75 percent by weight, compared to the amount of nitrosamine formed in the comparative solid oral pharmaceutical composition that is free of said nitrosamine inhibitor.

Clause 12: The solid oral pharmaceutical composition of any of clauses 1 to 11, wherein the amount of nitrosamine formed in the solid oral pharmaceutical composition is reduced by at least 80 percent by weight, compared to the amount of nitrosamine formed in the comparative solid oral pharmaceutical composition that is free of said nitrosamine inhibitor.

Clause 13: The solid oral pharmaceutical composition of any of clauses 1 to 12, wherein the amount of nitrosamine formed in the solid oral pharmaceutical composition is reduced by at least 80 percent by weight, or at least 85 percent by weight, or at least 90 percent by weight, or at least 95 percent by weight, in each case compared to the amount of nitrosamine formed in the comparative solid oral pharmaceutical composition that is free of said nitrosamine inhibitor.

Clause 14: The solid oral pharmaceutical composition of any of clauses 1 to 13, wherein the amount of nitrosamine formed in the solid oral pharmaceutical composition is reduced by from 92 percent by weight to less than or equal to 100 percent by weight, or by 93 percent by weight to less than or equal to 98 percent by weight, compared to the amount of nitrosamine formed in the comparative solid oral pharmaceutical composition that is free of said nitrosamine inhibitor.

Clause 15: The solid oral pharmaceutical composition of any one of clauses 1 to 14, wherein the nitrosamine inhibitor is introduced into the solid oral pharmaceutical composition by at least one of an intra-granular method or an extra-granular method.

Clause 16: The solid oral pharmaceutical composition of any one of clauses 1 to 15, wherein the pharmaceutically acceptable excipient comprises at least one of a diluent, a binder, a compression aid, a granulating agent, a disintegrant, a glidant, or a lubricant.

Clause 17: The solid oral pharmaceutical composition of any one of clauses 1 to 16, wherein the pharmaceutically acceptable excipient comprises at least one of microcrystalline cellulose, sucrose, hydroxypropyl cellulose, hydroxypropyl methylcellulose, sodium starch glycolate, starch, xylitol, fructose, sorbitol, calcium phosphate, calcium sulfate, magnesium stearate, oleic acid, stearic acid, stearyl alcohol, calcium carbonate, dextrose, lactose, polyvinylpyrrolidone, crosslinked polyvinylpyrrolidone, silica, titanium dioxide, gelatin, or triglercerides.

Clause 18: The solid oral pharmaceutical composition of any one of clauses 1 to 17, wherein the solid oral pharmaceutical composition is in a form selected from tablets, capsules, and free flowing granules.

The present invention is more particularly described in the following examples, which are intended to be illustrative only, since numerous modifications and variations therein will be apparent to those skilled in the art. Unless otherwise specified, all parts and all percentages are by weight.

EXAMPLES

In Part 1 of the following examples, there is described the preparation and evaluation of comparative solid oral pharmaceutical compositions and those according to the present invention, which include different levels of n-propyl 3,4,5-trihydroxybenzoate as the nitrosamine inhibitor. In Part 2 of the following examples, there is described the preparation and evaluation of comparative solid oral pharmaceutical compositions and those according to the present invention, in which n-propyl 3,4,5-trihydroxybenzoate was added intra-granularly and extra-granularly. In Part 3 of the following examples, there is described the preparation and evaluation of comparative solid oral pharmaceutical compositions and those according to the present invention that were evaluated over 3 months at 40° C., and for 1 month at 50° C.

Part-1

Solid oral pharmaceutical compositions according to the present invention (Ex's 1-4) were prepared by dissolving n-propyl 3,4,5-trihydroxybenzoate in ethanol, which was added onto microcrystalline cellulose (AVICEL PH 102 obtained commercially from DuPont) (MCC) followed by drying in an oven at 40° C. for 4 hours, to form n-propyl 3,4,5-trihydroxybenzoate loaded MCC. The n-propyl 3,4,5-trihydroxybenzoate loaded MCC was added to sertraline and microcrystalline cellulose (AVICEL PH 102) in amounts appropriate to provide n-propyl 3,4,5-trihydroxybenzoate levels of 0.1 percent by weight, 0.5 percent by weight, 1 percent by weight, and 2 percent by weight, where the percent weights in each case are based on the weight of sertraline. The comparative example (CE-1) was prepared in accordance with Ex's 1-4, but no n-propyl 3,4,5-trihydroxybenzoate was added thereto. The comparative (CE-1) and inventive (Ex's 1-4) solid oral pharmaceutical compositions: included sertraline and microcrystalline cellulose in a weight proportion of 1.25:1; were granulated and tabulated using the same process and under the same conditions to form test samples; and were evaluated by liquid chromatography-mass spectrometry (LC-MS) to determine initial (to) amounts of nitroso-sertraline. The comparative and inventive test samples were then subjected to 70° C. at ambient % RH, with samples being withdrawn and evaluated at 3 and 6 days to determine the amount of nitroso-sertraline formed by LC-MS analysis. The results are summarized in the following Table 1, and graphically in FIG. 1 of the drawings. In FIG. 1, the term "PG" means n-propyl gallate (i.e., n-propyl 3,4,5-trihydroxybenzoate).

TABLE 1

| Example | % n-propyl 3,4,5-trihydroxybenzoate | Day 0 Nitroso-Sert[(1)] (ppm) | Day 3 Nitroso-Sert (ppm) | Day 6 Nitroso-Sert (ppm) |
|---|---|---|---|---|
| CE-1 | 0.0 | 0.34 | 3.56 | 3.46 |
| Ex-1 | 0.1 | 0.28 | 2.15 | 2.58 |
| Ex-2 | 0.5 | 0.11 | 1.01 | 0.74 |
| Ex-3 | 1.0 | 0.08 | 0.57 | 0.60 |
| Ex-4 | 2.0 | 0.06 | 0.15 | 0.16 |

[(1)]Nitroso-sertraline.

With reference to Table 1, for day 3, the solid oral pharmaceutical compositions of inventive Ex's 1-4 each were determined to have a percent (by weight) reduction in the formation of nitroso-sertraline, relative to the amount/weight of nitrosamine formed in comparative CE-1 of: 39.5%; 71.6%; 84.1%; and 95.8%, respectively. With further reference to Table 1, for day 6, the solid oral pharmaceutical compositions of inventive Ex's 1-4 each were determined to have a percent (by weight) reduction in the formation of nitroso-sertraline, relative to the amount/weight of nitrosamine formed in CE-1 of: 25.6%; 78.8%; 82.7%; and 95.4%, respectively.

Part-2

Figure 2:
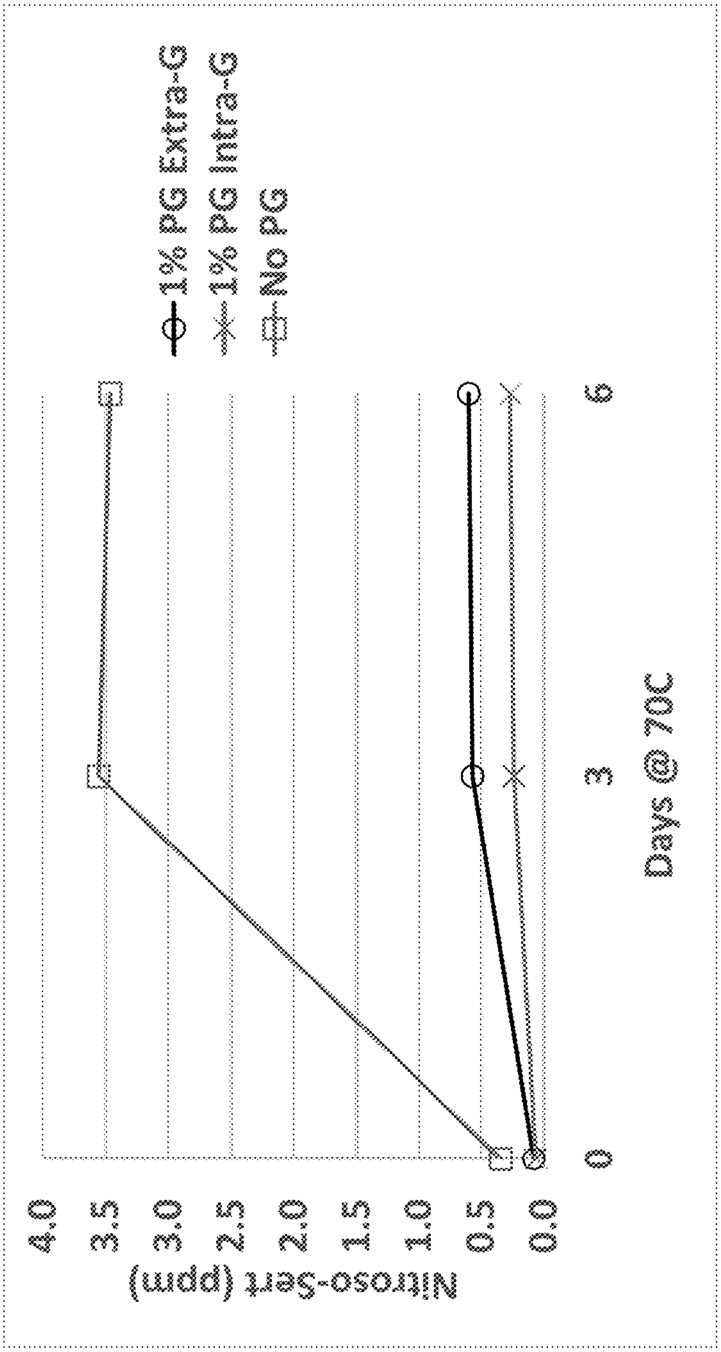
FIG. 2 is a graphical representation of a plot of nitrososertraline formed in a comparative solid oral pharmaceutical composition and solid oral pharmaceutical compositions according to the present invention that were prepared intragranularly and extra-granularly, and as described in further detail in the Examples.

In the following comparative (CE-1) and inventive (Ex's 5 and 6) examples sertraline and microcrystalline cellulose (AVICEL PH 102 obtained commercially from DuPont) (MCC) were present in a weight ratio of 1.25:1. Inventive Example 6 (Ex-6) corresponds to and was prepared as described with regard to Ex-3 in Part-1. The composition of inventive Ex-5 was prepared by dissolving n-propyl 3,4,5-trihydroxybenzoate in ethanol, with water q.s., which was then added (by spray application) intra-granularly to hydroxypropyl cellulose (HPC) and sertraline, so as to provide 1 percent by weight of n-propyl 3,4,5-trihydroxybenzoate, based on weight of sertraline (with MCC being subsequently added after high shear granulation and fluid bed drying). The comparative example (CE-1) included no n-propyl 3,4,5-trihydroxybenzoate, and was the same as comparative example (CE-1) of Part-1. The comparative (CE-1) and inventive test samples (Ex's 5 and 6) were evaluated by LC-MS to determine initial (to) amounts of nitroso-sertraline. The comparative and inventive test samples were then subjected to 70° C. at ambient % RH, with samples being withdrawn and evaluated at 3 and 6 days to determine the amount of nitroso-sertraline formed by LC-MS analysis. The results are summarized in the following Table 2, and graphically in FIG. 2 of the drawings. In FIG. 2, the term "PG" means n-propyl gallate (i.e., n-propyl 3,4,5-trihydroxybenzoate). In FIG. 2: the term "Extra-G" means the n-propyl 3,4,5-trihydroxybenzoate was added extra-granularly; and the term "Intra-G" means the n-propyl 3,4,5-trihydroxybenzoate was added intra-granularly.

TABLE 2

| Example | % n-propyl 3,4,5-trihydroxybenzoate | Day 0 Nitroso-Sert[(1)] (ppm) | Day 3 Nitroso-Sert (ppm) | Day 6 Nitroso-Sert (ppm) |
|---|---|---|---|---|
| CE-1 | 0.0 | 0.34 | 3.56 | 3.46 |
| Ex-5[(2)] | 1.0 | 0.06 | 0.24 | 0.27 |
| Ex-6[(3)] | 1.0 | 0.08 | 0.57 | 0.60 |

[(1)]Nitroso-sertraline.
[(2)]Intra-granular.
[(3)]Extra-granular.

With reference to Table 2, for day 3, the solid oral pharmaceutical compositions of inventive Ex's 5 and 6 each were determined to have a percent (by weight) reduction in the formation of nitroso-sertraline, relative to the amount/weight of nitrosamine formed in comparative CE-1 of: 93.3%; and 84.0%, respectively. With further reference to Table 2, for day 6, the solid oral pharmaceutical compositions of inventive Ex's 5 and 6 each were determined to have a percent (by weight) reduction in the formation of nitroso-sertraline, relative to the amount/weight of nitrosamine formed in CE-1 of: 92.2%; and 82.7%, respectively. The results as summarized in Table 2 and depicted graphically in FIG. 2. demonstrate that solid oral pharmaceutical compositions according to the present invention provide similarly desirable results, with regard to reduced formation of nitroso-sertraline, whether the n-propyl 3,4,5-trihydroxybenzoate is introduced into the composition intra-granularly or extra-granularly.

Part-3

In this Part-3: a comparative solid oral pharmaceutical composition (CE-1) containing no n-propyl 3,4,5-trihydroxybenzoate; and an inventive solid oral pharmaceutical composition (Ex-7) containing 1 percent by weight of n-propyl 3,4,5-trihydroxybenzoate, based on based on weight of sertraline, were each prepared in accordance with the descriptions provided in Part-1 with regard to CE-1 and Ex-3, respectively.

Figure 3:
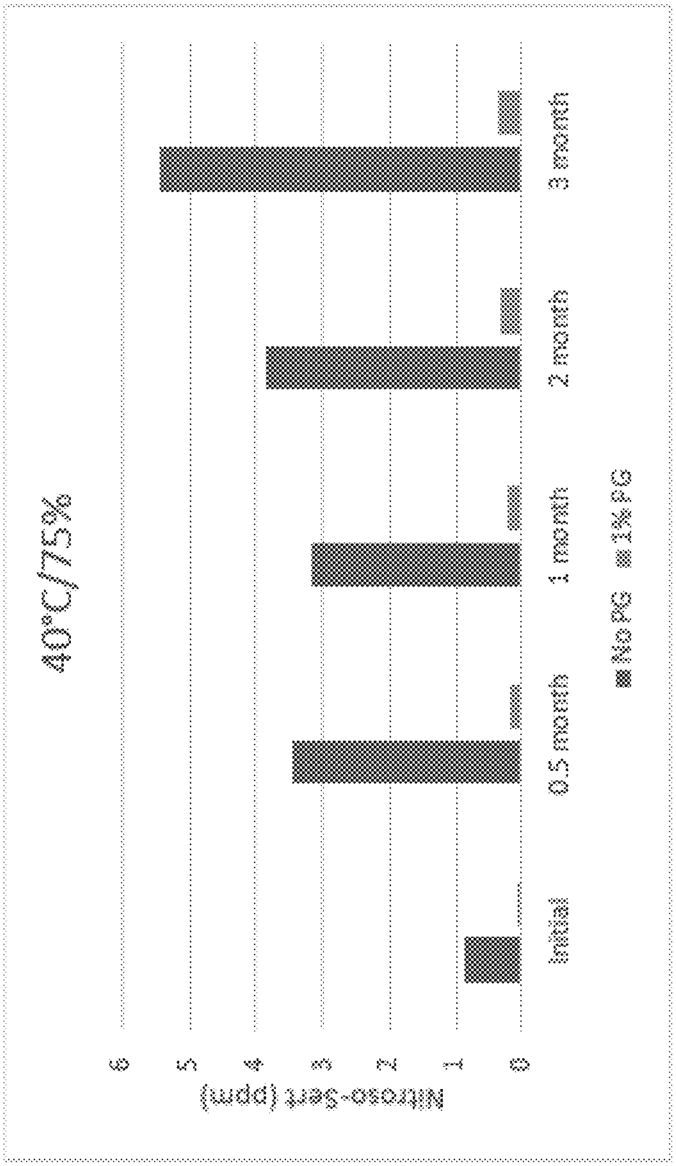
FIG. 3 is a graphical representation of a plot of nitrososertraline formed in a comparative solid oral pharmaceutical composition and a solid oral pharmaceutical composition according to the present invention over a period of 3 months at 40° C./75% RH, as described in further detail in the Examples.

The comparative (CE-1) and inventive (Ex-7) solid oral pharmaceutical compositions were evaluated by LC-MS to determine initial (to) amounts of nitroso-sertraline. The comparative (CE-1) and inventive (Ex-7) test samples were then subjected to 40° ° C. at 75% RH, with samples being withdrawn and evaluated at 0.5 months, 1 month, 2, months, and 3 months, to determine the amount of nitroso-sertraline formed by LC-MS analysis. The results are summarized in the following Table 3, and graphically in the bar graph of FIG. 3 of the drawings. In FIG. 3, the term "PG" means n-propyl gallate (i.e., n-propyl 3,4,5-trihydroxybenzoate); and the term "Nitroso-Sert" means Nitroso-sertraline.

TABLE 3

| Example | % PG[(4)] | Day 0 N-Sert[(5)] (ppm) | 0.5 Months N-Sert (ppm) | 1 month N-Sert (ppm) | 2 months N-Sert (ppm) | 3 months N-Sert (ppm) |
|---|---|---|---|---|---|---|
| CE-1 | 0.0 | 0.86 | 3.46 | 3.18 | 3.86 | 5.43 |
| Ex-7 | 1.0 | 0.08 | 0.17 | 0.20 | 0.32 | 0.34 |

[(4)]"PG" means n-propyl gallate (i.e., n-propyl 3,4,5-trihydroxybenzoate).
[(5)]"N-Sert" means Nitroso-sertraline.

With reference to Table 3, the inventive solid oral pharmaceutical composition (Ex-7) was determined to have a percent (by weight) reduction in the formation of nitroso-sertraline, relative to the amount/weight of nitrosamine formed in comparative CE-1 of: 95.1% at 0.5 months; 93.7% at 1 month; 91.7% at 2 months; and 93.7% at 3 months.

Figure 4:
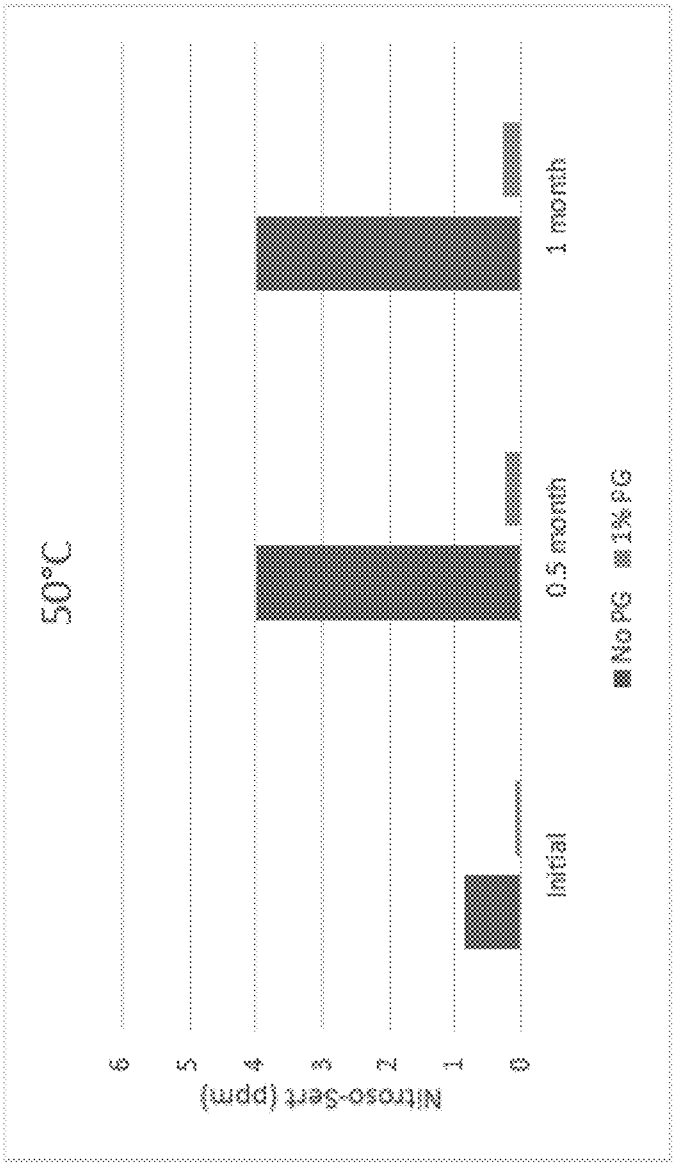
FIG. 4 is a graphical representation of a plot of nitrososertraline formed in a comparative solid oral pharmaceutical composition and a solid oral pharmaceutical composition according to the present invention over a period of 1 month at 50° C. and ambient humidity, as described in further detail in the Examples.

The comparative (CE-1) and inventive (Ex-7) solid oral pharmaceutical compositions were evaluated by LC-MS to determine initial (to) amounts of nitroso-sertraline. The comparative (CE-1) and inventive (Ex-7) test samples were then subjected to 50° C. at ambient % RH, with samples being withdrawn and evaluated at 0.5 months and 1 month, to determine the amount of nitroso-sertraline formed by LC-MS analysis. The results are summarized in the following Table 4, and graphically in the bar graph of FIG. 4 of the drawings. In FIG. 4, the term "PG" means n-propyl gallate (i.e., n-propyl 3,4,5-trihydroxybenzoate); and the term "Nitroso-Sert" means Nitroso-sertraline.

TABLE 4

| Example | % PG[(4)] | Day 0 N-Sert[(5)] (ppm) | 0.5 Months N-Sert (ppm) | 1 month N-Sert (ppm) |
|---|---|---|---|---|
| CE-1 | 0.0 | 0.86 | 3.99 | 4.01 |
| Ex-7 | 1.0 | 0.08 | 0.23 | 0.28 |

[(4)]"PG" means n-propyl gallate (i.e., n-propyl 3,4,5-trihydroxybenzoate).
[(5)]"N-Sert" means Nitroso-sertraline.

With reference to Table 4, the inventive solid oral pharmaceutical composition (Ex-7) was determined to have a percent (by weight) reduction in the formation of nitrososertraline, relative to the amount/weight of nitrosamine formed in comparative CE-1 of: 94.2% at 0.5 months; and 93.0% at 1 month.

The present invention has been described with reference to specific details of particular embodiments thereof. It is not intended that such details be regarded as limitations upon the scope of the invention except insofar as to the extent that they are included in the accompanying claims.

What is claimed is:

1. A solid oral pharmaceutical composition comprising:

(a) an active pharmaceutical ingredient;

(b) a nitrosamine inhibitor comprising linear or branched $C_1$-$C_{10}$ alkyl 3,4,5-trihydroxybenzoate; and (c) a pharmaceutically acceptable excipient, wherein at least one of, (i) said active pharmaceutical ingredient comprises at least one covalently bonded amine group that is subject to conversion to nitrosamine; or (ii) said solid oral pharmaceutical composition comprises at least one amine that is subject to conversion to nitrosamine, and wherein said nitrosamine inhibitor is present in an amount at least sufficient to reduce the amount of nitrosamine formed in said solid oral pharmaceutical composition, compared to the amount of nitrosamine formed in a comparative solid oral pharmaceutical composition that is free of said nitrosamine inhibitor.

2. The solid oral pharmaceutical composition of claim 1, wherein said active pharmaceutical ingredient comprises at least one of, an angiotensin II receptor blocker, a beta-blocker, a histamine H2-receptor antagonist, a selective serotonin reuptake inhibitor, or pharmaceutically acceptable salts of one or more thereof.

3. The solid oral pharmaceutical composition of claim 1, wherein said active pharmaceutical ingredient comprises at least one covalently bonded amine group that is subject to conversion to nitrosamine.

4. The solid oral pharmaceutical composition of claim 3, wherein said active pharmaceutical ingredient comprises at least one of sertraline, or a pharmaceutically acceptable salt of sertraline.

5. The solid oral pharmaceutical composition of claim 1, wherein said nitrosamine inhibitor comprises linear or branched $C_2$-$C_5$ alkyl 3,4,5-trihydroxybenzoate.

6. The solid oral pharmaceutical composition of claim 1, wherein said nitrosamine inhibitor comprises n-propyl 3,4,5-trihydroxybenzoate.

7. The solid oral pharmaceutical composition of claim 1, wherein said amount of said nitrosamine inhibitor is at least 0.05 percent by weight, based on weight of said active pharmaceutical ingredient.

8. The solid oral pharmaceutical composition of claim 7, wherein said amount of said nitrosamine inhibitor is from 0.05 percent by weight to 4 percent by weight, based on weight of said active pharmaceutical ingredient.

9. The solid oral pharmaceutical composition of claim 8, wherein, said amount of said nitrosamine inhibitor is from 0.5 percent by weight to 3 percent by weight, based on weight of said active pharmaceutical ingredient.

10. The solid oral pharmaceutical composition of claim 1, wherein the amount of nitrosamine formed in said solid oral pharmaceutical composition is reduced by at least 50 percent by weight, compared to the amount of nitrosamine formed in said comparative solid oral pharmaceutical composition that is free of said nitrosamine inhibitor.

11. The solid oral pharmaceutical composition of claim 1, wherein the amount of nitrosamine formed in said solid oral pharmaceutical composition is reduced by at least 75 percent by weight, compared to the amount of nitrosamine formed in said comparative solid oral pharmaceutical composition that is free of said nitrosamine inhibitor.

12. The solid oral pharmaceutical composition of claim 1, wherein the amount of nitrosamine formed in said solid oral pharmaceutical composition is reduced by at least 80 percent by weight, compared to the amount of nitrosamine formed in said comparative solid oral pharmaceutical composition that is free of said nitrosamine inhibitor.

13. The solid oral pharmaceutical composition of claim 1, wherein said nitrosamine inhibitor is introduced into said solid oral pharmaceutical composition by at least one of an intra-granular method or an extra-granular method.

14. The solid oral pharmaceutical composition of claim 1, wherein said pharmaceutically acceptable excipient comprises at least one of microcrystalline cellulose, sucrose, hydroxypropyl cellulose, hydroxypropyl methylcellulose, sodium starch glycolate, starch, xylitol, fructose, sorbitol, calcium phosphate, calcium sulfate, magnesium stearate, oleic acid, stearic acid, stearyl alcohol, calcium carbonate, dextrose, lactose, polyvinylpyrrolidone, crosslinked polyvinylpyrrolidone, silica, titanium dioxide, gelatin, or triglercerides.

15. The solid oral pharmaceutical composition of claim 1, wherein said solid oral pharmaceutical composition is in a form selected from tablets, capsules, and free flowing granules.

* * * * *